United States Patent [19]

Hansen et al.

[11] Patent Number: 5,552,146
[45] Date of Patent: Sep. 3, 1996

[54] METHODS AND COMPOSITIONS RELATING TO USEFUL ANTIGENS OF *MORAXELLA CATARRHALIS*

[75] Inventors: Eric J. Hansen, Plano; Merja Helminen; Isobel Maciver, both of Dallas, all of Tex.

[73] Assignee: Board of Regents, The University of Texas System, Austin, Tex.

[21] Appl. No.: 745,591

[22] Filed: Aug. 15, 1991

[51] Int. Cl.$^6$ .......................... A61K 39/95; A61K 39/02; A61K 39/40; C07K 14/22

[52] U.S. Cl. ..................... 424/251.1; 424/184.1; 530/350

[58] Field of Search .................. 424/88, 92, 184.1, 424/251.1; 530/350; 435/69.1

[56] References Cited

FOREIGN PATENT DOCUMENTS

WO90/12114 of 1990 WIPO .............................. C12Q 1/68

OTHER PUBLICATIONS

Murphy, T. F., "Studies of the Outer Membrane Proteins of *Branhamella catarrhalis*," Am. J. Med., 88(suppl. 5A):41S–45S, 1990.

Goldblatt et al., "*Branhamella cattarhalis*: Antigenic Determinants and the Development of the IgG Subclass Response in Childhood," J. Infect. Dis., 162:1128–1135, 1990.

Consensus, Paediatr. Infect. Dis. J. 8(1):S94–S97, 1989.

Murphy & Loeb, "Isolation of the outer membrane of *Branhamella catarrhalis*," Microbial Pathogenesis, 6:159–174, 1989.

Murphy, T. F., "The surface of *Branhamella catarrhalis*: a systematic approach to the surface antigens of an emerging pathogen," Paediatr. Infect. Dis. J. 8(1):S75–S77, 1989.

Murphy & Bartos, "Surface–Exposed and Antigenically Conserved Determinants of Outer Membrane Proteins of *Branhamella catarrhalis*," Infect. Immun. 57(10):2938–2941, 1989.

Bartos & Murphy, "Comparison of the Outer Membrane Proteins of 50 Strains of *Branhamella catarrhalis*," J. Infect. Dis. 158(4):761–765, 1988.

Eliasson, I., "A Protein Antigen Characteristic of *Branhamella catarrhalis*," Acta Path. Micribiol. Scand. Sect. B., 88:281–286, 1980.

Dialog Search Report.

Beaulieu & Roy, "Construction of a Species–Specific DNA Probe for *Branhamella catarrhalis*," 89th Annual Meeting of the American Society for Microbiology, New Orleans, Louisiana, USA, May 14–18, 1989. Abstr. Annu. Meet. Am. Soc. Microbiol. 89 (0). 1989. p. 124, Abstract #D–249.

Bhushan & Murphy, "Molecular Characterization of Outer Membrane Protein E. of *Branhamella catarrhalis*: a Potential Vaccine Candidate," 91st General Meeting of the American Society for Microbiology 1991, Dallas, Texas, USA, May 5–9, 1991. Abstr. Gen. Meet. Am. Soc. Microbiol. 91 (0). 1991. p. 57, Abstract #B–191.

Black & Wilson, "Immunoglobulin G (IgG) Serological Response to *Branhamella catarrhalis* in Patients with Acute Bronchopulmonary Infections," J. Clin. Pathol., 41:329–333, (1988).

Chapman et al., "Development of Bacterial Antibody During *Branhamella catarrhalis* Infection," J. of Infect. Dis., 151(5):878–882, (1985).

Helminen et al, Infect & Imm 61:2003–2010, 1993.

Doyle et al Reditr. Infect Dis Journ 8:545–47 1989.

Hanson, M. S. et al., 1989, Expression of the Heat–Modifiable Major Outer Membrane Protein of *Haemophilus influenzae* Type b is Unrelated to Virulence, Infection and Immunity, 57 (6):1639–1646.

Klingman, K. L. and Murphy, T. F., 1992, Identification and purification of the lipooligosaccharide–associated high molecular weight outer membrane protein (HMW–OMP) of *Branhamella catarrhalis*, Abstract of the 92nd General Meeting of the American Society for Microbiology, p. 90, B–388.

Shenep, J. L., et al., 1983, Further Studies of the Role of Noncapsular Antibody in Protection Against Experimental *Haemophilus influenzae* Type b Bacteremia, Infection and Immunity 42(1):257–263.

Srikumar, R., et al., 1992, Monoclonal antibodies specific to porin of *Haemophilus influenzae* type b: localization of their cognate epitopes and test of their biological activities, Molecular Microbiology 6(5):665–676.

Yogev, R. and Hansen, E. J., 1987, Dissociation of Virulence and Protection from Infection by Mutant Analysis in *Haemophilus influenzae* Type b, Infection and Immunity 55(8):1944–1947.

*Primary Examiner*—Hazel F. Sidberry
*Attorney, Agent, or Firm*—Arnold, White & Durkee

[57] ABSTRACT

The present disclosure relates to selected antigenic proteins obtained from the outer membranes of *Moraxella catarrhalis*, that have been found by the inventors to have a variety of useful properties. These proteins, termed OMPs ("Outer Membrane Proteins"), are characterized as having molecular weights of 30, 80 and 100 kD, respectively. Studies set forth herein demonstrate that monoclonal antibodies directed against these proteins confer a protective effect against infection by *Moraxella catarrhalis* organisms in animal models, demonstrating the potential usefulness of such antibodies in conferring passive immunity as well as the potential usefulness of these OMPs, or variants thereof, in the preparation of vaccines. Also disclosed are DNA segments encoding these OMPs, methods for preparing the antigens, or variants, through the application of recombinant DNA techniques, as well as diagnostic methods and embodiments.

7 Claims, 2 Drawing Sheets m    4B7    3HB    10F3    B
10F3

METHODS AND COMPOSITIONS RELATING TO USEFUL ANTIGENS OF *MORAXELLA CATARRHALIS*

BACKGROUND OF THE INVENTION

1. Field of the Invention

The present invention relates generally to various outer membrane proteins (OMPs) of *Moraxella catarrhalis* which have been found by the inventors to be useful targets in immunotherapy, such as in the preparation of vaccines or protective antibodies for use in treatment of *Moraxella catarrhalis*-related diseases. In particular aspects, the present invention concerns antigens identified by molecular weights of 30, 80 and 100 kD, recombinant clones encoding these antigens, antigen fragments derived therefrom, equivalents thereof, as well as to antibodies reactive with these species. Further, the invention concerns methods for the detection of *Moraxella catarrhalis* antigens and antibodies, as well as the use of specific antigens both in passive and active immunity against *Moraxella catarrhalis* infections.

2. Description of the Related Art

It was previously thought that *Moraxella catarrhalis* (previously known as *Branhamella catarrhalis* or *Neisseria catarrhalis*) was a harmless saprophyte of the upper respiratory tract. However, during the previous decade, it has been determined that this organism is an important human pathogen. In fact, recent studies have established this Gram-negative diplococcus as the cause of a number of human infections (Murphy, 1989). For example, *Moraxella catarrhalis* is a leading cause of otitis media, acute maxillary sinusitis as well as generalized infections of the lower respiratory tract (see, e.g., Murphy et al., 1989). Studies have established that the incidence of otitis media and sinusitis attributed to *Moraxella catarrhalis* infections is increasing, with it being about the third most common causative organism. In fact, reports have identified otitis media as the most common disease for which infants and children receive health care (Consensus, 1989).

The "Consensus" report referred to above concluded that prevention of otitis media is an important health care goal due to both its occurrence in infants and children, as well as certain populations of all age groups. In fact, the total financial burden of otitis media has been estimated to be at least 2.5 billion annually, or approximately 3% of the health care budget. Vaccines were identified as the most desired approach to the prevention of this disease for a number of reasons. For example, it was estimated that if vaccines could reduce the incidence of otitis media by 30%, this outcome could bring about an annual health care savings of at least $400 million. However, while some progress has been made in the development of vaccines for 2 of the 3 common otitis media pathogens, *Streptococcus pneumoniae* and *Haemophilus influenzae*, there is no indication that similar progress has been made with respect to *Moraxella catarrhalis*. This is particularly troublesome in that *Moraxella catarrhalis* now accounts for approximately 17–20% of all otitis media infection (Murphy, 1989).

Previous attempts have been made to identify and characterize *Moraxella catarrhalis* antigens that would serve as potentially important targets of the human immune response to infection (Murphy, 1989; Goldblatt et al., 1990; Murphy et al., 1990). Generally speaking, the surface of *Moraxella catarrhalis* is composed of outer membrane proteins (OMPs), lipooligo-saccharide (LOS) and fimbriae. As Murphy points out, *Moraxella catarrhalis* appears to be somewhat distinct from other gram-negative bacteria in that attempts to isolate the outer membrane of this organism using detergent fractionation of cell envelopes has generally proven to be unsuccessful in that the procedures did not yield consistent results. Moreover, preparations were found to be contaminated with cytoplasmic membranes which suggest an unusually characteristic of the *Moraxella catarrhalis* cell envelope.

However, workers in the field have demonstrated the existence of 7 or 8 major OMP species, and these appear to be fairly consistent from *Moraxella catarrhalis* strain to strain, in spite of the great diversity of stains tested. For example, Campagnari et al. has identified the OMPs by letters A–H beginning with a band of molecular weight 98 Kd (OMP-A) and proceeding to the band with a molecular weight of about 21 Kd (OMP-H). (Campagnari et al., 1987).

The LOS of *Moraxella catarrhalis* has also been suggested as a possible target for vaccine development. LOS has been isolated from *Moraxella catarrhalis* strains and subjected to SDS-PAGE and silver staining (Murphy, 1989). It was reported that all but one strain produced an identical pattern of LOS staining. Thus, it appears that the LOS of *Moraxella catarrhalis* is very highly antigenically conserved, thus raising the feasibility of using a portion of the LOS molecule as a vaccine component.

Lastly, the Fimbriae have been suggested as a possible vaccine candidate. Fimbriae apparently play a role in adherence and colonization of mucosal services in some bacteria. Workers in the field have postulated that if antigenically conserved epitopes are expressed on fimbriae and can be identified, then it is possible that antibodies to such epitopes might be useful therapeutically, or that such epitopes can serve as vaccine components.

Unfortunately, although various subcomponents of the *Moraxella catarrhalis* cell have been suggested as places to begin a search for vaccine candidates, there has still been no such candidate identified. Certainly, no antigenic epitope or epitopes have been shown to induce protective antibodies. Thus, it is clear that there is currently a need to identify which, if any, *Moraxella catarrhalis* component may serve as useful antigens that can, for example, be employed in the preparation of both passive and active immunotherapeutic reagents such as vaccines. Additionally, once such an antigen or antigens is identified, there is a need for providing methods and compositions which will allow the preparation of these vaccines and quantities that will allow their use on a wide scale basis in therapeutic protocols.

SUMMARY OF THE INVENTION

Accordingly, in a general and overall sense, the present invention is concerned with the identification and subsequent preparation of an *Moraxella catarrhalis* antigen species that would be of use both in the prevention and diagnosis of disease. In more particular terms, the invention concerns the inventors' surprising discovery that particular *Moraxella catarrhalis* OMP antigens, including the 30, 80 and 100 Kd OMP antigens, have particular utility in vaccine development. It is postulated by the inventors, therefore, these antigens can be used directly as a component of a vaccine, or can be employed for the preparation of corresponding or equivalent antigen through sequence analysis.

It should be pointed out that of these OMP antigens, the inventors believe that the 30 and 100 kD species will prove to be the most useful, in that their studies have shown that antibodies directed against these two OMP species are broadly reactive with *Moraxella catarrhalis* subtypes and isolates. However, antibodies against the 80 kD species have not, as yet, been shown to react with all subspecies, and thus may not be pan-reactive. Thus, particularly preferred embodiments of the invention concern the 30 and 100 kD OMP antigens, DNA fragments encoding these antigens and related species, antibodies recognizing these antigen species, and the like.

In certain embodiments, the present invention thus concerns an antigen composition comprising a purified protein or peptide antigen incorporating an epitope that is immunologically cross-reactive with one or more of the foregoing *M. catarrhalis* OMP antigens. While, generally, the purified protein or peptide antigen will comprise the OMP itself, the present disclosure provides techniques which may be employed for preparing variants of these OMP antigens, peptides that incorporate related antigenic epitopes, as well as antigenic functional equivalents of each of these. Furthermore, in that DNA segments encoding the various OMP antigens are disclosed, the antigens may be provided essentially free of antigenic epitopes from other *M. catarrhalis* antigens through the application of recombinant technology. That is, one may prepare the antigen by recombinant expression means using a host cell other than *M. catarrhalis* or related species, and thereby provide the antigen in an essentially pure antigenic state, with respect to other *M. catarrhalis* antigens. Such preparations will therefore be free, e.g., of LOS or fimbriae antigens.

In still further embodiments, through the use of standard DNA sequencing technology, DNA segments disclosed herein may be sequenced, and from this DNA sequence one may determine the underlying amino acid sequence of the selected OMP protein, whether it be the 30, 80 or 100 kD species. Once this information is obtained, identification of suitable antigenic epitopes is a relatively straightforward matter through the use of, for example, software programs for the prediction of such epitopes that are available to those of skill in the art. The amino acid sequence of these "epitopic core sequences" may then be readily incorporated into shorter peptides, either through the application of peptide synthesis or recombinant technology. Preferred peptides will generally be on the order of 15 to 50 amino acids in length, and more preferably about 15 to about 30 amino acids in length. It is proposed that shorter antigenic peptides which incorporate epitopes of the selected OMP will provide advantages in certain circumstances, for example, in the preparation of vaccines or in immunologic detection assays. Exemplary advantages include the ability to circumvent problems of contamination and purity often associated with proteins prepared by recombinant production in that peptides of this length may be prepared readily be synthetic means using peptide synthesizers.

In other embodiments, the present invention concerns processes for preparing compositions which include purified protein or peptide antigens that incorporate epitopes that are immunologically cross-reactive with the 30, 80 or 100 kD OMP. In a general sense, these processes include first selecting cells that are capable of expressing such a protein or peptide antigen, culturing the cells under conditions effective to allow expression of the antigen, and collecting the antigen to thereby prepare the composition. Where one desires to prepare the OMP antigen itself, one will simply desire to culture *M. catarrhalis* cells as a first step. In this case, the antigen will be provided, upon expression, in the outer membrane fraction of the cell. The antigen is then prepared by, first, preparation of membrane fraction followed by solubilization and extraction of the antigen from the prepared membranes using an ionic or nonionic detergent. Further purification may be achieved by a variety of methods including column fractionation, isoelectric focusing, and the like, or even immunoadsorption employing OMP-directed antibodies.

Of course, in light of the disclosure herein one may choose more preferred embodiments to prepare the desired antigen that include expressing a recombinant DNA segment encoding the antigen in a recombinant host cell. Preferred recombinant host cells for expression of antigens in accordance with the invention will typically be a bacterial host cell in that the antigen is a bacterial antigen. Preferred bacterial host cells include *E. coli, H. influenzae*, Salmonella species, Mycobacterium species, or even *Bacillus subtilis* cells. Of course, where desired, one may also express the desired antigen or antigens in eukaryotic cells.

As indicated above, in particular embodiments, the present invention concerns DNA segments which encode the desire protein or peptide antigen. Methods are disclosed herein for obtaining such segments in a purified state relative to their naturally occurring state. These DNA segments will have a number of advantages and uses. For example, segments encoding the entire OMP gene may be introduced into recombinant host cells and employed for expressing the entire protein antigen. Alternatively, through the application of genetic engineering techniques, subportions or derivatives of the selected OMP gene may be employed to prepare shorter peptide sequences which nevertheless incorporate the desired antigenic epitopes. Furthermore, through the application of site-directed mutagenesis techniques, one may re-engineer DNA segments of the present invention to alter the coding sequence, e.g., to introduce improvements to the antigenicity of epitopic core sequences and thereby prepare antigenically functional equivalent peptides. Of course, where desired, one may also prepare fusion peptides, e.g., where the antigen coding regions are aligned within the same expression unit with other desired antigen or proteins or peptides having desired functions, such as for immunodetection purposes (e.g., enzyme label coding regions).

Depending on the host system employed, one may find particular advantages where DNA segments of the present invention are incorporated into appropriate vector sequences which may, e.g., improve the efficiency of transfection of host cells. Where bacterial host cells are employed, it is proposed that virtually any vector known in the art to be appropriate for the selected host cell may be employed. Thus, in the case of *E. coli*, one may find particular advantages through the use of plasmid vectors such as pBR322, or bacteriophages such as λGEM-11. Other particular examples are disclosed hereinbelow.

In the preparation of recombinant clone banks from which appropriately transfected cells are selected, it will generally be the case that expression of the selected OMP gene sequences can be achieved in such host cells without the use of vectors having their own intrinsic promoter sequences. This is because the genomic *M. catarrhalis* DNA fragments employed for clone bank preparation will include endogenous promoters associated with the various coding sequences. However, the inventors propose that one may ultimately desire to re-engineer the promoter region of the antigen-coding fragments of the present invention to introduce heterologous promoter. This may allow one to overexpress the OMP antigen in relation to its natural expression by *M. catarrhalis* cells.

It is contemplated that nucleic acid segments of the present invention will have numerous uses other than in connection with expression of antigenic peptides or proteins. For example, nucleic acid segments of at least 14 or so nucleotides in length that incorporate regions of the OMP gene sequence may be employed as selective hybridization probes for the detection of *M. catarrhalis* sequences in selected samples or, e.g., to screen clone banks to identify clones which comprise corresponding or related sequences. Furthermore, short segments may be employed as nucleic acid primers, such as in connection with PCR technology, for use in any of a number of applications, including, e.g., cloning and engineering exercises, or in PCR-based detection protocols.

In still further embodiments, the invention concerns the preparation of antibodies capable of immunocomplexing with epitopes of the OMP antigen. Particular techniques for preparing antibodies in accordance with the invention are disclosed hereinbelow. However, it is proposed by the inventors that any of the current techniques known in the art for the preparation of antibodies in general may be employed, through the application of either monoclonal or polyclonal technology. As noted above, a surprising aspect of the invention involves the inventors' discovery that monoclonal antibodies directed against the 30, 80 and 100 kDa OMP antigens provide a protective effect against *M. catarrhalis* challenge in animal models. This surprising finding indicates not only that antibodies may be employed in the preparation of compositions for use in connection with passive immunotherapy, but further, that epitopes of these OMP antigens may be employed in the preparation of vaccine compositions. Accordingly, the present invention is directed both to vaccine compositions which include an antigen in accordance with the present invention, or antibodies against such an antigen, together with a pharmaceutically acceptable carrier, diluent, or adjuvant.

In still further embodiments, the present invention concerns immunodetection methods and associated kits. It is proposed that antigens of the present invention may be employed to detect antibodies having reactivity therewith, or, alternatively, antibodies prepared in accordance with the present invention, may be employed to detect antigens. In general, these methods will include first obtaining a sample suspected of containing such an antigen or antibody, contacting the sample with an antibody or antigen in accordance with the present invention, as the case may be, under conditions effective to allow the antibody to form an immunocomplex with the antigen or antibody to be detected, and detecting the presence of the antigen in the sample by detecting the formation of an immunocomplex. In general, the detection of immunocomplex formation is quite well known in the art and may be achieved through the application of numerous approaches. For example, the present invention contemplates the application of ELISA, RIA, immunoblot, dotblot, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the antigen or antibody sought to be detected, as the case may be, may be employed. Exemplary samples include clinical samples obtained from a patient such as blood or serum samples, ear swabs, sputum samples, middle ear fluid or even perhaps urine samples may be employed. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of antigens and/or antibodies in a sample. Generally speaking, kits in accordance with the present invention will include a suitable OMP antigen (i.e., either the 30, 80 or 100 kD species, or protein containing epitopes corresponding to one or more of these species), or antibody directed against such an antigen, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

DETAILED DESCRIPTION OF THE PREFERRED EMBODIMENTS

Figure 1:
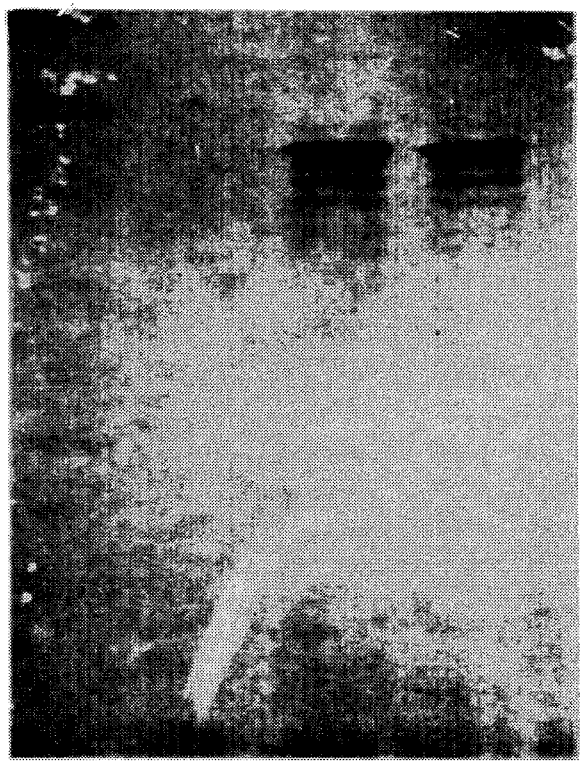
FIG. 1. Western blot analysis of *M. catarrhalis* proteins using as a probe monoclonal antibody 10F3, which recognizes the 80 kD OMP. Lane A is a Rainbow protein molecular weight marker (M.W. 14.3 to 200 kD, Amersham); Lane B is a negative control comprising a whole cell lysate of 4B1/pBR322/RR1 (4B1 is an *M. catarrhalis* gene encoding an unrelated protein recognized by monoclonal antibody 4B1); Lanes C and D are whole cell lysates of 10F3/pBR322/RR1; and Lane E is a blank control.

The present invention relates to the inventors' identification of particular outer membrane proteins (OMPs) of *Moraxella catarrhalis* that are found to have particularly useful properties, e.g., in the preparation of both diagnostic and therapeutic reagents. These proteins appear to be cell surface-exposed in their natural state, and exhibit molecular weights of about 30, 80 and 100 kilodaltons, respectively, upon SDS-PAGE. Particular embodiments relate to the recombinant cloning of sequences encoding these proteins, antigenic subfragments, variants, and the like. The present invention also relates to monoclonal antibodies to these *M. catarrhalis* OMPs that are shown to reduce the number of infecting *M. catarrhalis* bacteria present in localized lung infections, as demonstrated in pulmonary clearance studies using a murine model system.

Recombinant clones, expressing one or more of the selected OMPs, and that may be used to prepare purified OMP antigens as well as mutant or variant protein species in significant quantities, are included within the scope of the disclosure. The selected OMP antigen, and variants thereof, are anticipated to have significant utility in diagnosing and treating *M. catarrhalis* infections. For example, it is proposed that these OMP antigens, or peptide variants, may be used in immunoassays to detect *M. catarrhalis* or as a vaccine to treat *M. catarrhalis* infections.

As those skilled in the art will appreciate, the nucleic acid sequences which encode for the selected OMP antigen, or their variants, may be useful in hybridization or polymerase chain reaction (PCR) methodology to detect *M. catarrhalis*. Accordingly, included in the present invention disclosure is information which may be used to prepare a wide variety of DNA fragments having a number of potential utilities, such as the preparation of relatively short immunogenic/antigenic peptidyl subfragments of the antigen, the use of DNA or RNA sequences in PCR and hybridization studies as probes for in vitro detection, as well as other useful medical and biomedical applications related to the research, diagnosis and treatment of *M. catarrhalis* infections.

The OMP antigens of the present invention are referred to, respectively, as the 30, 80 and 100 kD OMPs. These proteins have been identified by the inventors by reference to monoclonal antibodies that were selected from a battery of monoclonal antibodies against *M. catarrhalis* outer membrane vesicles. These antibodies were employed as Western blot probes to identify corresponding antigens from SDS-PAGE runs of *M. catarrhalis* 035E outer membrane vesicle preparations. The monoclonal antibody recognizing the 30 kD OMP is termed 8B6, the antibody recognizing the 80 kD OMP is termed 10F3, and that recognizing the 100 kD antigen has been designated 17C7 (see FIGS. 1 through 3). Importantly, each of the foregoing hybridomas have been shown to be protective against *M. catarrhalis* infection in animal models.

The present invention envisions various means for both producing and isolating the OMP antigen proteins of the present invention, ranging from isolation of purified or partially purified protein from natural sources (e.g., from *M. catarrhalis* bacterial cells), or from recombinant DNA sources (e.g., *E. coli* or microbial cells). In the latter case, the OMP antigens of the invention, or antigenic peptides derived therefrom, may be provided in essentially antigenically pure states in that they will be free of other *M. catarrhalis* epitopes unrelated to the selected OMP species.

It is proposed that isolation of the OMP antigen from either natural or recombinant sources in accordance with the invention may be achieved isolating cell envelopes or outer membranes and then using a detergent-based purification scheme. In the case of recombinant cells, the desired antigen may be present in inclusion bodies.

Since monoclonal antibodies to the 30, 80 and 100 kD OMP antigens are disclosed by the present invention, the use of immunoabsorbant techniques are anticipated to be useful in purifying the OMP antigen, or its immunologically cross reactive variants. It is proposed that useful antibodies for this purpose may be prepared generally by the techniques disclosed hereinbelow, or as in generally known in the art for the preparation of monoclonals (see, e.g., U.S. Pat. Nos. 4,514,498 and 4,740,467), and those reactive with the desired OMP protein or peptides selected. Moreover, it is believed that the foregoing general isolation scheme will work equally well for isolation of OMP variants or of antigenic/immunogenic subfragments of the protein, requiring only the generation and use of antibodies having affinity for the desired peptidyl region.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or underlying DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

Epitopic Core Sequences of the OMP Antigens

As noted above, it is proposed that particular advantages may be realized through the preparation of synthetic peptides which include epitopic/immunogenic core sequences. These epitopic core sequences are identified herein in particular aspects as hydrophilic regions of the OMP antigen. It is proposed that these regions represent those which are most likely to promote T-cell or B-cell stimulation, and, hence, elicit specific antibody production. An epitopic core sequence, as used herein, is a relatively short stretch of amino acids that is "complementary" to, and therefore will bind, antigen binding sites on OMP-directed antibodies. Additionally or alternatively, an epitopic core sequence is one that will elicit antibodies that are cross-reactive with OMP directed antibodies. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired OMP antigen with the corresponding OMP-directed antisera.

In general, the size of the polypeptide antigen is not believed to be particularly crucial, so long as it is at least large enough to carry the identified core sequence or sequences. The smallest useful core sequence anticipated by the present disclosure would be on the order of about 15 amino acids in length. Thus, this size will generally correspond to the smallest peptide antigens prepared in accordance with the invention. However, the size of the antigen may be larger where desired, so long as it contains a basic epitopic core sequence.

Accordingly, through the use of computerized peptide sequence analysis program (DNAStar Software, DNAStar, Inc., Madison, Wis.), the inventor proposes to identify particular hydrophilic peptidyl regions of the 30, 80 or 100 kD OMP antigen which are believed to constitute epitopic core sequences comprising particular epitopes of the protein.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Antigenically Functional Equivalent Amino Acids

As noted above, it is believed that numerous modifications and changes may be made in the structure of the desired OMP antigen, or antigenic/immunogenic subportions thereof, and still obtain a molecule having like or otherwise desirable characteristics.

It is, for example, known that certain amino acids may be substituted for other amino acids in a protein structure in order to modify or improve its antigenic or immunogenic activity (see, e.g., Kyte et al, or Hopp, U.S. Pat. No. 4,554,101, incorporated herein by reference). For example, through the substitution of alternative amino acids, small conformational changes may be conferred upon an antigenic peptide which result in increase affinity between the antigen and the antibody binding regions. Alternatively, amino acid substitutions in certain OMP antigenic peptides may be utilized to provide residues which may then be linked to other molecules to provide peptide-molecule conjugates which retain enough antigenicity of the starting peptide to be useful for other purposes. For example, a selected OMP peptide bound to a solid support might be constructed which would have particular advantages in diagnostic embodiments.

The importance of the hydropathic index of amino acids in conferring interactive biologic function on a protein has been discussed generally by Kyte et al. (1982), wherein it is found that certain amino acids may be substituted for other amino acids having a similar hydropathic index or core and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules. Preferred substitutions for monitoring binding capability will generally involve amino acids having index scores within 2 units of one another, and more preferably within 1 unit.

TABLE I

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, will preferably be exchanged with an amino acid such as valine (+4.2) or leucine (+3.8). Alternatively, at the other end of the scale, lysine (−3.9) will preferably be substituted for arginine (−4.5), and so on.

Accordingly, these amino acid substitutions are generally based on the relative similarity of R-group substituents, for example, in terms of size, electrophilic character, charge, and the like. In general, preferred substitutions which take various of the foregoing characteristics into consideration include the following:

TABLE II

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | leu; ala |
| Ser | thr |
| Thr | ser |
| Trp | tyr |
| Tyr | trp; phe |
| Val | ile; leu |

Preparation of Monoclonal Antibodies to *M. catarrhalis* OMPs

Monoclonal antibodies specific for the *Moraxella catarrhalis* OMPs of the present invention may be prepared using conventional immunization techniques. Initially, a composition containing antigenic epitopes of the OMP, such as an outer membrane vesicle preparation, can be used to immunize an experimental animal, such as a mouse, from which a population of spleen or lymph cells are subsequently obtained. The spleen or lymph cells can then be fused with cell lines, such as human or mouse myeloma strains, to produce antibody-secreting hybridomas. These hybridomas may be isolated to obtain individual clones which can then be screened for production of antibody to the desired OMP.

In particular aspects, the present invention utilizes outer membrane fragments from *M. catarrhalis* to induce an immune response in experimental animals. Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against outer membrane proteins. Hybridomas which produce monoclonal antibodies to the selected OMP are identified using standard techniques, such as ELISA and Western blot methods.

Hybridoma clones can then be cultured in liquid media and the culture supernatants purified to provide the OMP-specific monoclonal antibodies.

Use of Monoclonal Antibodies to OMP Antigens

In general, monoclonal antibodies to the desired OMP antigen of *M. catarrhalis* can be used in both the diagnosis and treatment of *M. catarrhalis* infections.

It is proposed that the monoclonal antibodies of the present invention will find useful application in standard immunochemical procedures, such as ELISA and Western blot methods, as well as other procedure which may utilize antibody specific to OMP epitopes. These OMP-specific monoclonal antibodies are anticipated to be useful in various ways for the treatment of *M. catarrhalis* infections through, for example, their application in passive immunization procedures.

Additionally, it is proposed that monoclonal antibodies specific to the particular OMP may be utilized in other useful applications. For example, their use in immunoabsorbent protocols may be useful in purifying native or recombinant OMP species or variants thereof.

Studies have shown that antibody preparations against the OMP antigens of the invention have a significant protective effect against *M. catarrhalis* infection. The present inventors have shown that passive immunization with monoclonal antibodies specific for these OMPs significantly reduce the numbers of *M. catarrhalis* organisms following a bolus injection of bacteria. This demonstrates that these OMP antigens may be employed in making gammaglobulin preparations for use in passive immunization against disorders associated with *M. catarrhalis* infections, or used directly as vaccine components.

To obtain suitable gammaglobulin preparations, one may desire to prepare monoclonal antibodies, preferably human or humanized hybridomas. Alternatively, it is proposed that one may desire to use globulin fractions from hyperimmunized individuals.

Recombinant Cloning Genes Encoding *M. catarrhalis* OMPs

The present invention also involves isolating *M. catarrhalis* OMP genes, or sequence variants, incorporating DNA segments encoding the 30, 80 or 100 kD OMP gene into a suitable vector, and transforming a suitable host, such that recombinant proteins, or variants thereof, are expressed. It will be appreciated by those of skill in the art that in light of the present disclosure the invention is also applicable to the isolation and use of the OMP gene sequences from any suitable source that includes appropriate coding sequences, such as any *M. catarrhalis* subspecies or isolate that expresses the desired OMP. Such sources may be readily identified by immunological screening with monoclonal antibodies to the selected OMP.

The preferred application of the present invention to the isolation and use of OMP-encoding DNA involves generally the steps of (1) isolation of Moraxella genomic DNA; (2) partial restriction enzyme digestion of the genomic DNA with an enzyme such as PstI, (the selected restriction enzyme is not crucial) to provide DNA having an average length of, e.g., 6 to 23 kb; (3) ligation of the partially digested DNA into a selected site within a selected vector, such as pBR322 (again, other plasmid or phage vectors may be used at this step, as desired); (4) transformation, transfection or electroporation of suitable host cells, e.g., *E. coli* cells, with the recombinant vector; and (5) selection of colonies expressing the desired OMP through the application of specifically designed screening protocols. Following identification of a clone which contains the OMP gene, one may desire to reengineer the gene into a preferred host/vector/promoter system for enhanced production of the outer membrane protein, or sequence variants thereof.

Through application of the foregoing general steps, the inventors have succeeded in identifying and selecting a number of clones which contain *M. catarrhalis* OMP genes in a manner which allows it to produce the corresponding outer membrane protein.

In a preferred application of these techniques, genomic DNA from *Moraxella catarrhalis* strain 035E was isolated from bacteria through the use of SDS, ribonuclease and proteinase K treatment, phenol/chloroform/isoamyl alchohol extraction and ethanol precipitation. Conditions were determined for achieving an appropriate partial restriction enzyme digestion, such as would provide fragments on the order of 6–23 kb in length, using a restriction enzyme, such as PstI. After size fractionation, the partially digested Moraxella DNA fragments of the selected size range were ligated with fully digested vector, such as pBR322, which was fully digested with PstI to generate compatible sites for ligation with the genomic DNA fragments.

Following the ligation, the recombinant vectors are then used to transform a suitable host, such as *E. coli* RR1, to produce a recombinant library having members that express *M. catarrhalis* protein species encoded by the DNA fragment inserts. The recombinant microbial clones are cultivated, preferably on the surface of a nutrient agar, to form visible colonies. Those colonies expressing surface-exposed *M. catarrhalis* outer membrane proteins are then identified using monoclonal antibodies to *M. catarrhalis* OMPs in a colony blot radioimmunoassay. Recombinant *E. coli* clones expressing proteins having epitopes reactive with anti-OMP antibodies may then be cultured in desired quantities.

Host Cell Cultures and Vectors

In general, of course, prokaryotes are preferred for the initial cloning of DNA sequences and constructing the vectors useful in the invention. For example, *E. coli* strain RR1 is particularly useful. Other microbial strains which may be used include *E. coli* strains such as *E. coli* LE392, *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F−, lambda−, prototrophic, ATCC No. 273325), bacilli such as *Bacillus subtilis*, or other enterobacteriaceae such as *Salmonella typhimurium* or *Serratia marcescens*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage lambda GEM™-11 may be utilized in making recombinant phage vector which can be used to transform host cells, such as *E. coli* LE392.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Sequencing of OMP Genes

After cloning the gene encoding the selected OMP, one will desire to perform restriction mapping and DNA sequence analysis, e.g., by the dideoxy method of Sanger et al. (1977). Both the DNA and the deduced amino acid sequence can then be compared with known sequences to determine homologies with known proteins. The amino acid sequence of the protein will reveal the nature of the various domains, e.g., cytoplasmic, membrane-spanning, and substrate binding domains, and give important information in terms of approaches to improving the structure of the enzyme through genetic engineering techniques.

Through the use of computerized peptide sequence analysis program (DNAStar Software, DNAStar, Inc., Madison, Wis.), particular hydrophilic peptidyl regions of the OMP antigen may be identified which are likely to constitute epitopic core sequences, comprising particular epitopes of the protein, as well as biologically functional equivalents of the foregoing peptides, as explained in more detail below.

Preparation of OMP Variants

Site-specific mutagenesis is a technique useful in the preparation of individual peptides, or biologically functional equivalent proteins or peptides, derived from the OMP antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagenesis in accordance herewith is performed by first obtaining a single-stranded vector which includes within its sequence a DNA sequence which encodes the OMP antigen. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected OMP gene using site-directed mutagenesis is provided as a means of producing potentially useful OMP species and is not meant to be limiting as there are other ways in which sequence variants of the OMP may be obtained. For example, recombinant vectors encoding the desired OMP gene may be treated with mutagenic agents to obtain sequence variants (see, e.g., a method described by Eichenlaub, 1979) for the mutagenesis of plasmid DNA using hydroxylamine.

Use of Nucleic Acid Sequences

As mentioned, in certain aspects, the DNA sequence information provided by the present disclosure allows for the preparation of relatively short DNA (or RNA) sequences having the ability to specifically hybridize to gene sequences of the selected OMP antigen gene. In these aspects, nucleic acid probes of an appropriate length are prepared based on a consideration of the natural sequence or derived from flanking regions of the OMP gene, such as regions downstream of the gene as found in plasmid pBR322. The ability of such nucleic acid probes to specifically hybridize to OMP gene sequences lend them particular utility in a variety of embodiments. Most importantly, the probes can be used in a variety of diagnostic assays for detecting the presence of pathogenic organisms in a given sample. However, other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 10 to 20, or so, nucleotide stretch of the sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having OMP gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

In that the OMP antigens of the present invention are believed to be indicative of pathogenic Moraxella species, the present invention will find particular utility as the basis for diagnostic hybridization assays for detecting OMP-specific RNA or DNA in clinical samples. Exemplary clinical samples that can be used in the diagnosis of infections are thus any samples which could possibly include Moraxella nucleic acid, including middle ear fluid, sputum, bronchoalveolar fluid, amniotic fluid or the like. A variety of hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of the corresponding OMP genes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated clones. In particular embodiments, mutant clone colonies growing on solid media which contain variants of the OMP sequence could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of the OMP gene may be utilized to identify those clones growing on solid media which contain sequence variants of the entire OMP gene. These clones can then be grown to obtain desired quantities of the variant OMP nucleic acid sequences or the corresponding OMP antigen.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as urease, alkaline phosphatase or peroxidase, instead of radioactive or other environmental undesirable reagents. In the case of enzyme tags, colorimetric indicator substrates are known which can be employed to provide a means visible to the human eye or spectrophoto-metrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., amniotic fluid, middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

In other embodiments, it is proposed that OMP sequences or variants thereof may be used to provide highly specific and sensitive detection of *M. catarrhalis* when used as reagents in polymerase chain reaction (PCR) assays. In general, by applying the PCR technology as set out, e.g., in U.S. Pat. No. 4,60,102, one may utilize various portions of the OMP sequence as oligonucleotide probes for the PCR amplification of a defined portion of OMP nucleic acid in a sample. The amplified portion of the OMP sequence may then be detected by hybridization with a hybridization probe containing a complementary sequence. In this manner, extremely small concentrations of *M. catarrhalis* nucleic acid may detected in a sample utilizing OMP sequences.

In other embodiments, OMP sequences may be utilized in PCR formats for the in vitro preparation of desired quantities of selected portions of the OMP gene. By amplifying selected gene portions of a selected OMP gene and then incorporating those portions into vectors, one can also prepare recombinant clones which express OMP variants, including subfragments of the OMP antigen. In this manner, peptides carrying antigen epitopes of the outer membrane protein may be prepared and utilized for various purposes.

Immunoassays

As noted, it is proposed that OMP peptides of the invention will find utility as immunogens, e.g., in connection with vaccine development, or as antigens in immunoassays for the detection of anti-OMP antigen-reactive antibodies. Turning first to immunoassays, in their most simple and direct sense, preferred immunoassays of the invention include the various types of enzyme linked immunosorbent assays (ELISAs) known to the art. However, it will be readily appreciated that the utility of OMP peptides is not limited to such assays, and that other useful embodiments include RIAs and other non-enzyme linked antibody binding assays or procedures.

In the preferred ELISA assay, peptides incorporating OMP antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human IgG. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethylbenzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Vaccine Preparation and Use

Immunogenic compositions, proposed to be suitable for use as a vaccine, may be prepared most readily directly from immunogenic OMP proteins and/or peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

EXAMPLE I

EDTA-Based Extraction of Outer Membrane Fragments

In order to obtain antibody to the OMP antigens, outer membrane fragments from *M. catarrhalis* strain 035E were prepared as an immunogen. *M. catarrhalis* strain 035E cells were grown on agar plates using brain heart infusion broth. Plates were incubated at 37° C. in a candle extinction jar. Outer membrane fragments were subsequently prepared from these cells by the EDTA-based extraction procedure of Murphy et al., *Microb. Path.*, 1989.

EXAMPLE II

Isolation of *M. catarrhalis* OMPs

In light of the present disclosure's identification of monoclonal antibodies specific to selected *M. catarrhalis* OMPs, it is proposed that the corresponding OMP antigen may be purified using the following general procedure. Cell envelopes will be prepared by sonication or outer membrane fragments will be extracted by EDTA-based treatment of whole *M. catarrhalis* cells. These membranes will be treated with ionic or non-ionic detergents to release the desired proteins which can then be purified by using conventional column chromatography or by immunoaffinity techniques.

EXAMPLE III

Preparation of Monoclonal Antibodies Specific for *M. catarrhalis* Outer Membrane Proteins The present example illustrates the steps employed by the inventors in reducing certain aspects of the invention to practice. In particular, this example relates to the generation and identification of hybridomas that produce monoclonal antibodies to the 30, 80 or 100 kD OMP antigen. Once hybridomas secreting monoclonal antibodies to surface-exposed OMP antigens from *M. catarrhalis* were identified, those determined to produce antibody to these OMP antigens were selected and cultured to produce antibody for use in other studies, such as those involving pulmonary clearance of *M. catarrhalis*.

BALB/c mice were immunized by intraperitoneal injection with outer membrane fragments of *M. catarrhalis* strain 035E prepared by the EDTA-based extraction procedure. Each animal was immunized with 50–100 µg protein in 0.1 ml of Freund's complete adjuvant. One month later, the animals were boosted with an identical quantity of this same protein preparation in incomplete Freund's adjuvant. Three weeks later, the mice were given an intravenous injection (into the tail vein) with 50 µg protein of the same membrane preparation suspended in PBS.

The "pancake" fusion method was employed as follows: $SP_{2/0}$-Ag14 plasmacytoma cells were employed. These cells were maintained in DMEM (Dulbecco's Modified Eagle Medium)/Penicillin-Streptomycin-Glutamine with 15% fetal bovine serum, 1% Fungizone and 8-azaguanine. Two weeks prior to the fusion, some of the cells were split into media with 1% Fungizone but lacking 8-azaguanine. These cells were maintained for 10 days at a density of no greater than $1-2\times10^5$/ml. Beginning three days before the fusion, $SP_{2/0}$ cells were subcultured every 24 hours and maintained at an approximate density of $2-3\times10^5$/ml. Three days before the fusion, the mice were boosted intravenously with about 50 µg of protein immunogen. On the day of the fusion, two mice were sacrificed by cervical dislocation. The spleens were removed aseptically and macerated. Spleen cells were collected in 10 mls of DMEM-HY media (60 ml NCTC-109, 6 tubes hypoxanthine-thymidine-glycine stock soln., 6 tubes oxalacetic acid-bovine insulin stock soln., 12 ml penicillin-streptomycin-glutamine, 2.7 ml 100 mM Na pyruvate, and 508 ml DMEM). At room temperature, $SP_{2/0}$ cells and spleen cells were collected by centrifugation at 170×g for 11 min. in their respective tubes. $SP_{2/0}$ cells and spleen cells were each resuspended in a total of 5 mls of DMEM-HY media.

The hypoxanthine-thymidine-glycine stock solution was prepared by adding 136 mg hypoxanthine to 100 ml 0.1M HCl, 38.7 mg thymidine to 100 ml $H_2O$, and 2.3 mg glycine to 20 ml $H_2O$. These solutions were dissolved separately, combined and then aliquoted into 2.2 ml volumes.

The oxalacetic acid-bovine insulin stock solution was prepared by dissolving 80.3 mg bovine insulin in 100 ml $H_2O$, adding 1.32 gm oxaloacetic acid and aliquoting into 1 ml. volumes.

Spleen cells were then diluted to $2\times10^8$ cells/5 mls and the $SP_{2/0}$ cells was diluted to $2\times10^7$ cells/5 mls. The ratio of spleen cells to $SP_{2/0}$ cells was 10:1. Spleen cells were then mixed with $SP_{2/0}$ cells in a ratio of 1:1. The spleen-$SP_{2/0}$ mixture was then treated with 3 mls of 50% PEG/DMEM-HY media for 35 sec. Fused spleen-$SP_{2/0}$ cells were washed immediately with DMEM-HY and incubated in 30% HY:HIFCS (35 ml DMEM-HY, 15 ml FBS, filter) for 24 hours at 37° C. 24 hours after the fusion, media and fused cells were collected in 20% HY:HIFCS (80 ml DMEM-HY, 20 ml FBS, filter) by centrifugation at 170×g for 5 min. The fused cells were then resuspended in 100 mls of 20% HAT:HIFCS and transferred to 96-well microtiter plates, 100 µl/well. One week after the fusion, 100 µl of 20% HY:HIFCS were added to each well. Two weeks after the fusion, when wells containing proliferating hybrid cells became acidic, each positive well was split into a 2 ml well on a 24-well plate and the culture supernatant assayed for antibody characterization.

Supernatants from these clones were screened for antibodies to *M. catarrhalis* by ELISA binding and Western blot methods using EDTA-extracted outer membrane fragments of *M. catarrhalis* strain 035E as antigen for the ELISA, and whole cell lysates of this strain as antigen for Western blots. Positive supernatants were then tested by the indirect antibody accessibility RIA to investigate the surface exposure of outer membrane antigens as described by Kimura et al. (1985 and 1986).

Positive hybridomas were then cultured in standard DME and the monoclonal antibodies were purified from culture supernatants on Protein A—Sepharose CL-4B as described by Ey et al., 1978.

Each Mab identified as being reactive with *M. catarrhalis* in Western blot analysis was used in the indirect antibody accessibility assay to determine if these Mabs were reactive with surface-exposed determinants of this organism. The antibody accessibility assay performed was described by Patrick et al., 1987.

Mab 10F3, which reacted with an antigen with an apparent MW of approximately 80,000 in Western blot analysis, was shown to bind to the surface of whole cells of strain 035E. This Mab reacted with 4 of 10 different *M. catarrhalis* strains tested in colony blot-RIA analysis by the method of Gulig et al., 1987. A culture deposit of hybridomas secreting Mab 10F3 has been made with the American Type Culture Collection as ATCC accession number HB 11092.

Mab 17C7 reacted with two different size bands in Western blot analysis. This Mab reacted with a band near the top of the gel that migrated in a diffuse form and sometimes with a second band that migrated with an apparent MW of 100,000. For the purpose of clarity, the Mab will be defined as being reactive with the 100,000 kD antigen. This Mab bound to the surface of strain 035E and reacted with all ten different *M. catarrhalis* strains tested in the colony blot RIA. A culture deposit of hybridomas secreting Mab 17C7 has been made with the American Type Culture Collection as ATCC accession number HB 11093.

Mab 8B6 reacted with an antigen with an apparent MW of approximately 30,000 in Western blot analysis. This Mab was also reactive with the surface of strain O35E and reacted with all ten different *M. catarrhalis* strains tested in the colony blot-RIA. A culture deposit of hybridomas Mab 8B6 has been made with the American Type Culture Collection as ATCC accession number HB 11091.

EXAMPLE IV

Pulmonary Clearance of *M. catarrhalis* using Monoclonal Antibodies Specific for the 30, 80 and 100 kD OMPs The present example illustrates steps employed by the inventors in reducing certain aspects of the invention to practice. This example demonstrates the ability of monoclonal antibodies to the 30, 80 and 100 kD OMPs to enhance pulmonary clearance of *M. catarrhalis* using a murine model system. Thus, this example demonstrates that antibodies to the 30, 80 or 100 kD OMP may be useful for passive immunization and that vaccines comprising these OMPs are likely to provide active immunity against *M. catarrhalis* infections.

A. Antibody Administration

Eighteen hours prior to bacterial challenge, groups of 5 mice were passively immunized by intravenous administration of monoclonal antibody 17C7, 8B6 or 10F3. Control animals were immunized with an irrelevant antibody, 2H11, which was directed against an outer membrane protein of *Haemophilus ducreyi*. Each animal received an equivalent amount of purified antibody corresponding to 150 μg of total protein.

B. Method of Bacterial Inoculation

Mice were anaesthetized by intramuscular injection of 2 mg of ketamine HCL (Fort Dodge Lab, Fort Dodge, Iowa) and 0.2 mg of acepromazine maleate (Fort Dodge Lab). After tracheal exposure each animal was intubated transorally with a 20 gauge intravenous catheter which was advanced until it could be visualized through the translucent tracheal wall. A PE-10 polyethylene tube containing 5 μl of bacterial suspension was then passed through the catheter into the lung where the bacteria were deposited with 150 μl of air. This technique delivered the inoculum to a localized, peripheral segment of the lung. In all experiments, mice were challenged with *M. catarrhalis* strain O35E.

C. Pulmonary Clearance

In each experiment, 5 mice were sacrificed by intraperitoneal injection of 0.75 mg of sodium pentobarbital (Abbott Labs, Chicago, Ill.) immediately after inoculation (0 h), to determine bacterial deposition in the lungs. At 6 hours after challenge, experimental (17C7-, 8B6- or 10F3-immunized) and control (2H11 immunized) groups were sacrificed, and the number of viable bacteria remaining in the lungs was determined as follows: the lungs from each animal were removed aseptically and homogenized in 2 ml of sterile BHI broth in a tissue homogenizer followed by grinding in a tissue grinder until smooth. The homogenate was serially diluted in BHI broth, plated on BHI agar and incubated at 37° C. in an air incubator with a 5% $CO_2$ atmosphere for 24 h. Clearance of *M. catarrhalis* from the lungs is expressed as the percentage of colony forming units (cfu) remaining in the lung at each time point compared with the mean cfu of bacteria present at 0 h in the same experiment.

RESULTS

The mean number of viable bacteria remaining in the lungs of immunized and control mice after bolus deposition of $0.98 \times 10^5$ to $2.0 \times 10^5$ cfu of *M. catarrhalis* O35E was determined and expressed as a percentage of the initial inoculum.

TABLE I

| Immunization | % of Bacteria Remaining at 6 h Post-Challenge | |
|---|---|---|
| Regimen | Expt. #1 | #2 |
| No immunization | 134 | 109 |
| 2H11 immunization | 113 | 108 |
| 17C7 immunization | 27 | 22 |
| 8B6 immunization | 32 | 45 |
| 10F3 immunization | 10 | 13 |

EXAMPLE V

Cloning the Gene Encoding the 80 kD OMP (10F3-Reactive) from *M. catarrhalis*

The present Example illustrates steps employed by the inventor in cloning the gene encoding for the 80 kD OMP from *M. catarrhalis*. The present Example discloses one or more preferred recombinant *E. coli* clones, expressing the 80 kD OMP antigen, isolated by the following procedures.

A. Isolation of genomic DNA

*M. catarrhalis* strain O35E was used as a representative Moraxella pathogen in this study. Genomic DNA from *M. catarrhalis* strain O35E was extracted and purified as follows. *M. catarrhalis* cells (approximately 2 gms wet weight) were scraped from agar plates and resuspended in 20 mls. PBS. To this suspension was added 3.2 ml 10% (w/v) SDS and 1 ml RNase (10 mg/ml). This mixture was incubated at 37° C., then 3 mg proteinase K added, followed by further incubation at 55° C. overnight. The incubated mixture was then extracted once with phenol, twice with phenol:chloroform:isoamyl alcohol, and three times with chloroform:isoamyl alcohol. The resulting DNA was then precipitated with two volumes of absolute ethanol, and collected with a Pasteur pipet.

B. Preparation of an *M. catarrhalis* genomic library in pBR322

The partial digestion of genomic DNA was achieved by incubating 100 μg portions of *M. catarrhalis* genomic DNA with varying amounts of the restriction enzyme PstI in a reaction volume of about 1.5 ml. at 37° C. for 1 hr. The partially digested genomic DNA was then size fractionated by sucrose density gradient centrifugation. Fractions containing DNA fragments from about 6 kb to 23 kb in length were selected and dialysed to obtain purified genomic DNA fragments for ligation with pBR322.

The plasmid vector pBR322 was fully digested with PstI by incubating 15 μg portions of pBR322 with 50 units of PstI in a 100 μl reaction volume at 37° C. for 18 hrs. Ligation of the purified DNA fragments into the PstI-digested pBR322 vector was accomplished by incubating 300 ng of the purified DNA fragments and PstI-digested pBR322 together with ATP and T4 DNA ligase under conditions described by Maniatis et al. (1982). After ligation, the DNA was diluted 1:5 with 10 mM TRis-HCl (pH 8.0) and was used to transform *E. coli* RR1 made competent by the $CaCl_2$ method.

C. Screening transformed RR1 colonies by colony blot-radioimmunoassay for *M. catarrhalis* OMP expression The colony blot RIA was accomplished as described by Gulig et al. (1987) with monoclonal antibody 10F3 as the primary antibody.

D. Characterising recombinant *E. coli* clones expressing *M. catarrhalis* OMP antigens Clones which reacted with monoclonal antibody 10F3 in the colony blot RIA were cultured using LB medium containing the antibiotic tetracycline (15 μg/ml). Whole cell lysates of recombinant *E. coli* RR1 expressing *M. catarrhalis* OMP antigens were prepared as described by Patrick et al., 1987. Briefly, portions of these whole-cell lysates were subjected to SDS-PAGE as described in Gulig et al., 1987, and then stained with Coomassie blue or transferred to nitrocellulose for Western blot analysis. The results are shown in FIG. 1 which indicate that recombinant 80 kD OMP gene is expressed in the clones identified by monoclonal antibody 10F3.

EXAMPLE VI

Cloning of the Genes Encoding the 30 kD (8B6-Reactive) and 100kD (17C7-Reactive) Outer Membrane Proteins of *M. catarrhalis*

A. Isolation of genomic DNA

*M. catarrhalis* genomic DNA was isolated from strain 035E as described above.

B. Preparation of a *M. catarrhalis* genomic DNA library using the bacteriophage vector λGEM-11

Purified *M. catarrhalis* DNA (100 μg) was partially digested with Sau3A (Promega Biotech) at room temperature as described above. The digested DNA was size-fractionated in sucrose density gradients and fragments of DNA 15 kb and larger were collected for use in library construction. These DNA fragments (1 μg) were filled in using the Klenow procedure (Promega) at 14° C. for 90 min. These fragments were then cleaned by standard procedures and ligated onto the phage DNA arms and packaged using the protocol and reagents supplied by Promega in the LambdaGEM—11* Xho I Half-Site Arms Cloning System, except that T4 DNA ligase from BRL was used. After packaging, the phage-based library was titered using *E. coli* LE392. This genomic library contained 50,000 recombinant clones.

C. Screening of the bacteriophage-based genomic DNA library with monoclonal antibodies 17C7 and 8B6

20,000 plaques were screened with Mabs 17C7 and 8B6 using the plaque screening procedure described in Current Protocols in Molecular Biology (Wiley Interscience) using radioiodinated goat anti-mouse Ig as the probe to detect Mabs bound to plaque material. One recombinant phage reactive with each Mab was ultimately identified.

D. Characterization of the recombinant phages reactive with Mabs 17C7 and 8B6

Liquid lysate cultures of these recombinant phage were prepared by the standard methods described in Current Protocols in Molecular Biology. The DNA was extracted using standard methods.

The recombinant phage reactive with Mab 17C7 had a DNA insert approximately 11 kb in size. The recombinant phage reactive with Mab 8B6 had a DNA insert approximately 18 kb in size.

Phage harvested from liquid lysates were heated at 100° C. for 3 min. in standard SDS digestion buffer and then used for SDS-PAGE and Western blot analysis to confirm that these recombinant phage were expressing the appropriate *M. catarrhalis* antigens.

Figure 2:
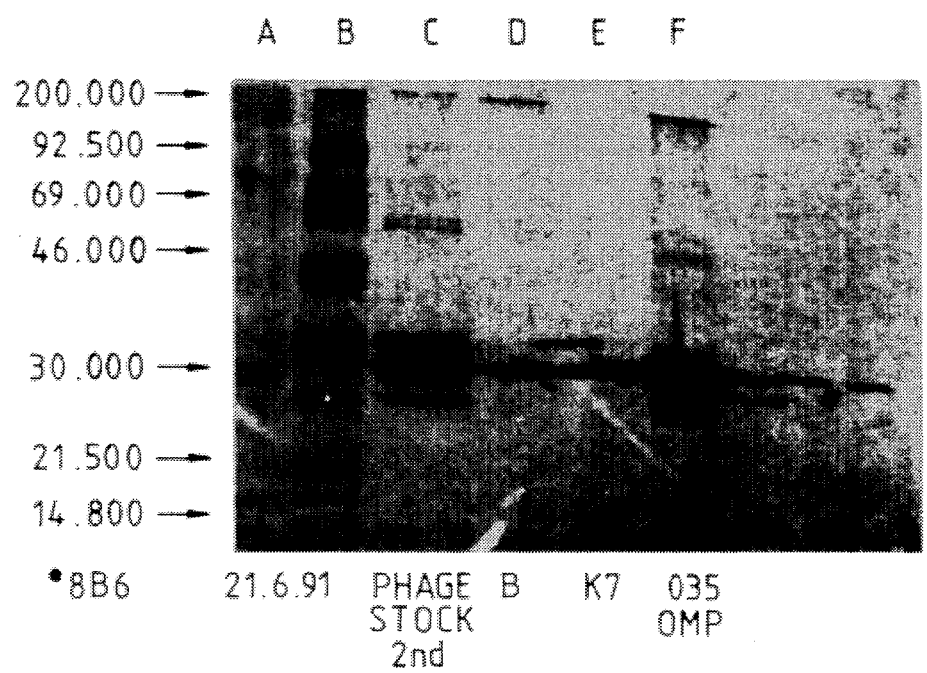
FIG. 2. Western blot analysis of *M. catarrhalis* proteins using as a probe monoclonal antibody 8B6, which recognizes the 30 kD OMP. Lane A is a Rainbow protein molecular weight marker (M.W. 14.3 to 200 kD, Amersham); Lane B is a prestained SDS-PAGE-standard, low molecular weight (M.W. 16 to 110 kD, Bio-Rad); Lane C contains proteins from a phage lysate of recombinant *E. coli* that express the 30 kD OMP (LE392/8B6); Lane D is a blank control; Lane E is a negative control (phage lysate from recombinant *E. coli* expressing the 100 kD OMP, LE392/17C7); and Lane F is a positive control (*M. catarrhalis* 035E outer membrane vesicles).

FIG. 2 is an illustrative Western blot analysis of proteins from *E. coli* clone LE392/8B6, which expresses the 30 kD OMP antigen. In this study, the various indicated samples were subjected to PAGE, transferred to a nitrocellulose membrane, and probed with the 30 kD OMP-specific monoclonal antibody 8B6. As can be seen, a band having an approximate molecular weight of 30 kD is seen in the LE 392/8B6 lane (lane C), and a similar band is seen in the positive control lane (lane F). The nature of the two additional bands seen in the LE 392/8B6 lane (lane C) is unclear, but they could be due to processing of the recombinant protein or overloading of the gel. The bands seen in the negative control lanes (lanes D and E) are clearly due to spillover from lanes C and F.

Figure 3:
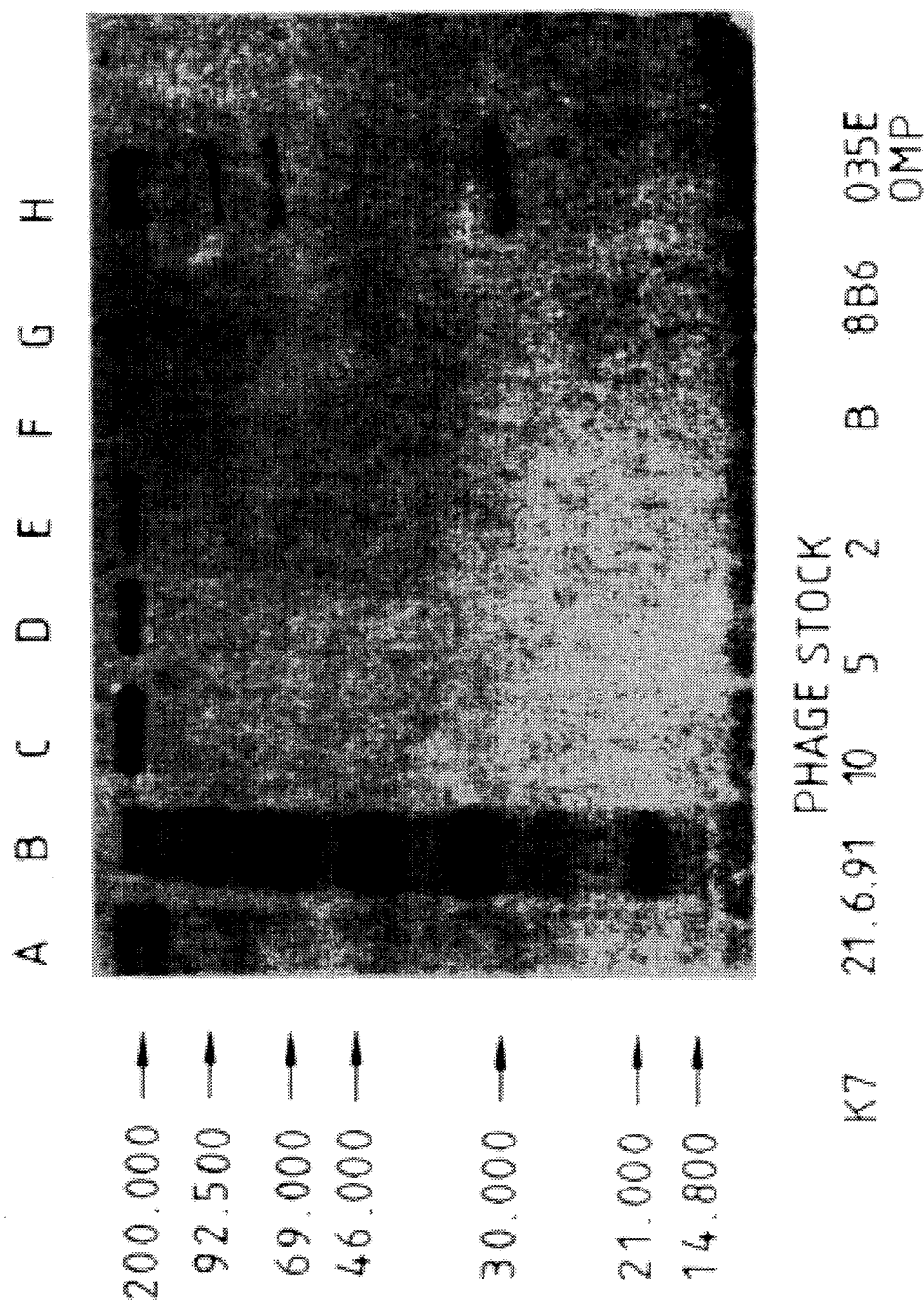
FIG. 3. Western blot analysis of *M. catarrhalis* proteins using as a probe monoclonal antibody 17C7, which recognizes the 100 kD OMP. Lane A is a Rainbow protein molecular weight marker (M.W. 14.3 to 200 kD, Amersham); Lane B is a prestained SDS-PAGE-standard, low molecular weight (M.W. 16 to 110 kD, Bio-Rad); Lanes C, D and E contain proteins from a phage lysate of recombinant *E. coli* that express the 100 kD OMP (LE392/17C7); Lane F is a blank control; Lane H is a negative control (phage lysate from recombinant *E. coli* expressing the 30 kD OMP, *E. coli*/8B6 phage lysate); and Lane G is a positive control (*M. catarrhalis* 035E outer membrane vesicles).

FIG. 3 shows a similar Western blot analysis of a phage lysate from a clone expressing the 100 kD OMP, designated LE 392/17C7, probed with monoclonal antibody 17C7. Lanes C–E comprise phage lysate proteins from clone LE392/17C7. These lanes exhibit slight reactivity in the 100 kD range, that comigrate with an apparently corresponding 100 kD band in the positive control (lane H). It is noted, however, that the majority of reactivity in the lysate samples migrated at an apparently higher molecular weight, possibly due to protein aggregation, lack of processing or a similar phenomenon.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting in kind or amount of the biological action. All such modifications are intended to be included within the scope of the appended claims.

REFERENCES

The following references, to the extent that they provide exemplary procedural or other details supplementary to those set forth herein, are specifically incorporated herein by reference.

Adelman et al. (1983) *DNA* 2:183
Bolivar et al. (1977) *Gene* 2:95
Campagnari et al. (1987), *Infect. Immun.*, 55:882–7
Chang et al. (1978) *Nature* 375:615
Consensus (1989), *Pediater. Infect. Dis. J.*, 8:S94-S97
Crea et al. (1978), *Proc. Natl. Acad. Sci. U.S.A* 75:5765
Eichenlaub, R. (1979) *J. Bacteriol* 138:559–566
EPO Appl. Publ. No. 0036776
Ey et al. (1978), *Immunochem* 5:429–436
Fiers et al. (1978) *Nature* 273:113
Goeddel et al. (1979) *Nature* 281:544
Goeddel et al. (1980) *Nucleic Acids Res.* 8:4057
Goldblatt et al. (1990), *Jrnl. Infect. Dis.*, 162:1128–1135
Gulig et al. (1987) *Infect. Immun.* 55:513–520
Hess et al. (1968) *J. Adv. Enzyme Reg.* 7:149
Hitzeman et al. (1980) *J. Biol. Chem.* 255:2073
Holland et al. (1978) *Biochemistry* 17:4900

Itakura et al. (1977) *Science* 198:1056
Jones (1977) *Genetics* 85:12
Kimura et al. (1986) *Infect. Immun.* 50:69–79
Kimura et al. (1985) *Infect. Immun.* 47:253–259
Kingsman et al. (1979) *Gene* 7:141
Kyte et al. (1982) *J. Mol. Biol.* 157:105–132.
Maniatis et al. (1982) *Molecular cloning: a laboratory manual* Cold Spring Harbor Laboratory, Cold Spring Harbor, N.Y.
Messing et al. *Third Cleveland Symposium on Macromolecules and Recombinant DNA*, Editor A. Walton, Elsevier, Amsterdam (1981)
Murphy (1989), *Pediat. Infect. Dis. J.*, 8:S75-S77
Murphy et al. (1989), *Microb. Path.*, 6:159–174
Murphy et al. (1990), *Am. Jrnl. Med.*, 88:5A-41S-5A-45S
Patrick et al. (1987), *Infect. Immun.*, 55:2902–2911
Sanger et al. (1977) *Proc. Natl. Acad. Sci.* USA 74:5463–5467
Stinchcomb et al. (1979) *Nature* 282:39
*Tissue Culture*, Academic Press, Kruse and Patterson, editors (1973)
Tschemper et al. (1980) *Gene* 10:157

What is claimed is:

1. An antigen composition comprising an *Moraxella catarrhalis* outer membrane antigen selected from the group consisting of *M. catarrhalis* outer membrane antigens immunologically reactive with monoclonal antibody 10F3 (ATCC HB 11092) or 17C7 (ATCC 11093), wherein said antigen is purified free of other *M. catarrhalis* outer membrane antigens.

2. The composition of claim 1, wherein the selected *M. catarrhalis* antigen is immunologically reactive with monoclonal antibody 10F3 (ATCC HB 11092).

3. The composition of claim 1, wherein the selected *M. catarrhalis* antigen is immunologically reactive with monoclonal antibody 17C7 (ATCC HB 11093).

4. The composition of claim 1, wherein the *M. catarrhalis* antigen is prepared by recombinant means.

5. The composition of claim 1, further defined as being essentially free of *M. catarrhalis* antigens other than those reactive with monoclonal antibody 10F3 or 17C7.

6. The composition of claim 1, wherein the antigen is comprised in a pharmaceutically acceptable buffer.

7. The composition of claim 6, wherein the pharmaceutically acceptable buffer includes an acceptable carrier or adjuvant.

* * * * *

UNITED STATES PATENT AND TRADEMARK OFFICE
CERTIFICATE OF CORRECTION

PATENT NO.    :   5,552,146

DATED         :   September 3, 1996

INVENTOR(S)   :   Eric J. Hansen et al.

It is certified that error appears in the above-identified patent and that said Letters Patent is hereby corrected as shown below:

Column 1, line 4, insert the following:

-- This invention was made with government support under NIH Grant Number AI23366. The government has certain rights in the invention. --

Signed and Sealed this

Fourth Day of April, 2000

Attest:

Q. TODD DICKINSON

Attesting Officer     Director of Patents and Trademarks